(12) United States Patent
Tourrel et al.

(10) Patent No.: US 10,549,095 B2
(45) Date of Patent: Feb. 4, 2020

(54) BINAURAL COCHLEAR IMPLANT SYSTEM

(71) Applicant: Oticon Medical A/S, Smørum (DK)

(72) Inventors: Guillaume Tourrel, Vallauris (FR); Frederic Bessoule, Vallauris (FR)

(73) Assignee: OTICON MEDICAL A/S, Smørum (DK)

( * ) Notice: Subject to any disclaimer, the term of this patent is extended or adjusted under 35 U.S.C. 154(b) by 158 days.

(21) Appl. No.: 15/819,429

(22) Filed: Nov. 21, 2017

(65) Prior Publication Data
US 2018/0140839 A1 May 24, 2018

(30) Foreign Application Priority Data

Nov. 22, 2016 (EP) ..................................... 16199925

(51) Int. Cl.
*A61N 1/36* (2006.01)
*A61N 1/375* (2006.01)
*A61N 1/05* (2006.01)

(52) U.S. Cl.
CPC ....... *A61N 1/36038* (2017.08); *A61N 1/0541* (2013.01); *A61N 1/37518* (2017.08)

(58) Field of Classification Search
CPC ............ A61N 1/36038; A61N 1/36036; A61N 1/0541; A61N 1/37518
See application file for complete search history.

(56) References Cited

U.S. PATENT DOCUMENTS

| 5,935,166 A * | 8/1999 | Kennedy ............ A61N 1/36036 600/25 |
|---|---|---|
| 2006/0173259 A1 | 8/2006 | Flaherty et al. |
| 2013/0041448 A1 | 2/2013 | Henshaw et al. |
| 2014/0214145 A1 | 7/2014 | Zimmerling et al. |

FOREIGN PATENT DOCUMENTS

| EP | 3 006 079 A1 | 4/2016 |
| WO | WO 2013/022444 A1 | 2/2013 |

\* cited by examiner

*Primary Examiner* — Alyssa M Alter
(74) *Attorney, Agent, or Firm* — Birch, Stewart, Kolasch & Birch, LLP

(57) ABSTRACT

According to an aspect, a binaural cochlear implant system is disclosed. The system includes an implantable stimulator; an ipsilateral cochlear implant electrode array connected to the stimulator and a lead connected to the stimulator at a first end of the lead and provided with a contralateral binaural cochlear implant electrode array at a second end of the lead, the lead being configured to be implanted beneath the skin above the skull of a hearing aid user, wherein the lead comprises at least one electrical wire connecting the contralateral binaural cochlear implant electrode array with the stimulator, and a reinforcement fiber running along length of the at least one electrical wire.

19 Claims, 8 Drawing Sheets

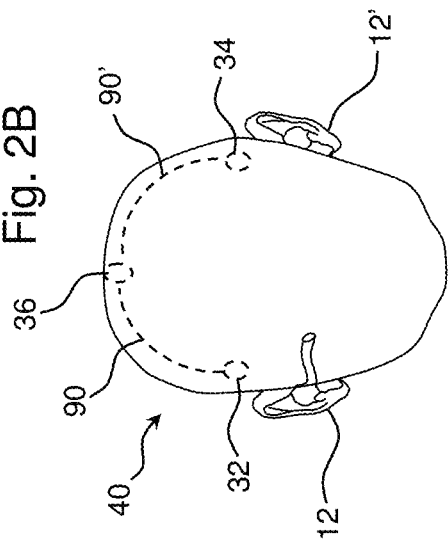
Fig. 2A
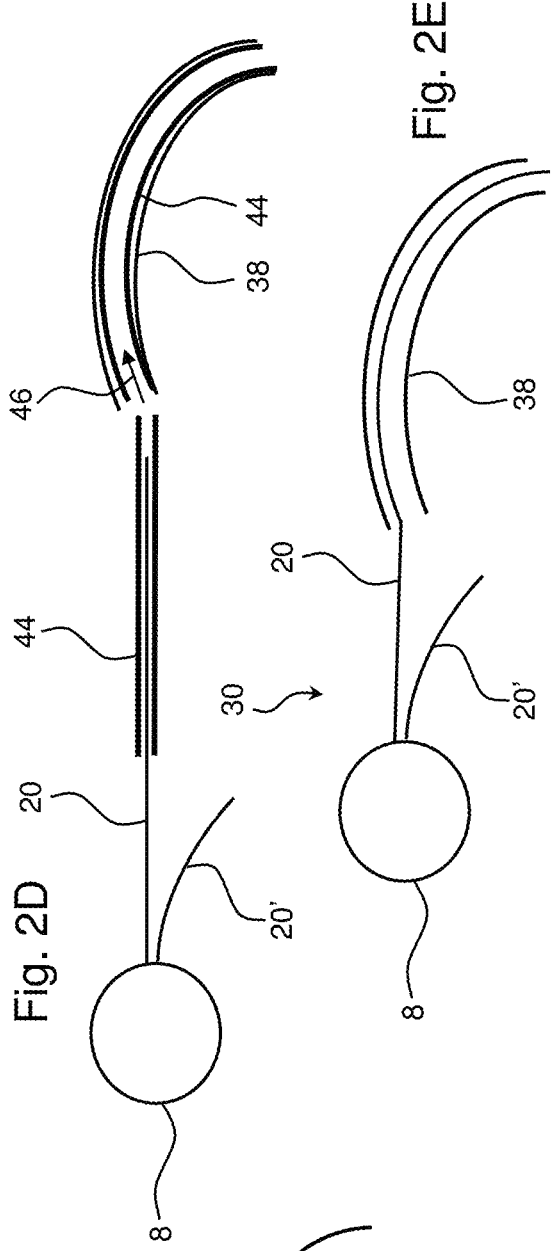
Fig. 2B
Fig. 2D
Fig. 2E
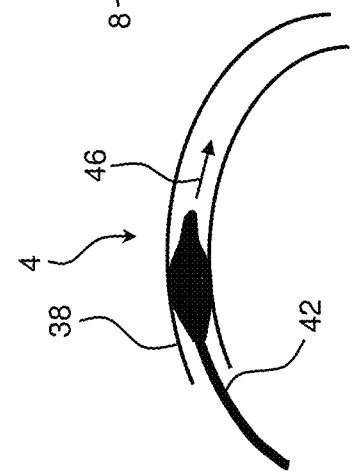
Fig. 2C

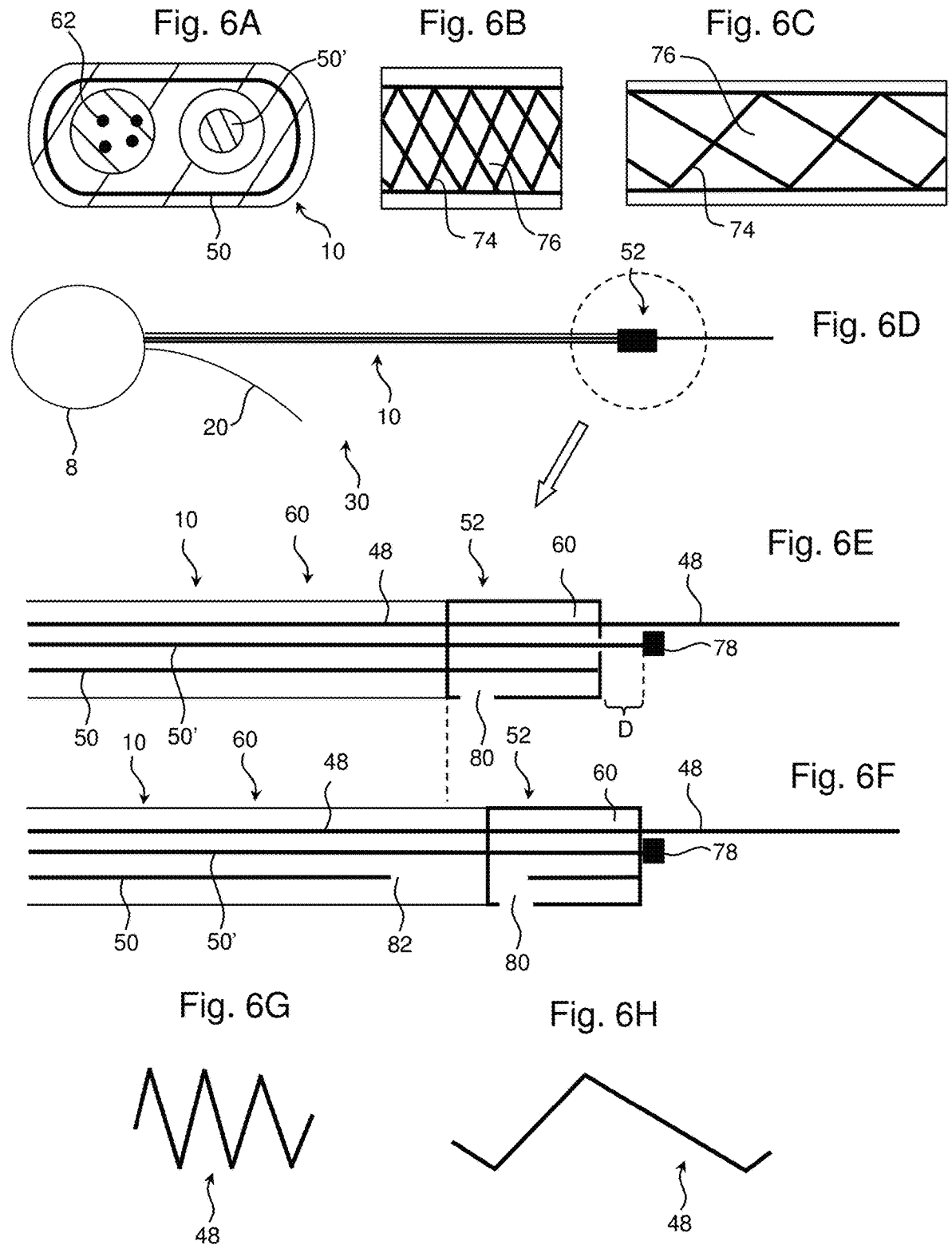

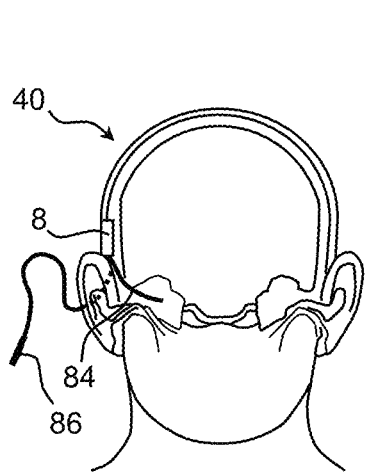
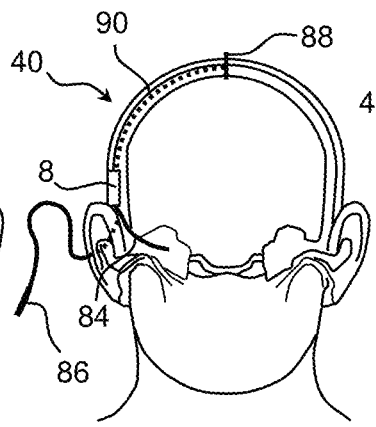
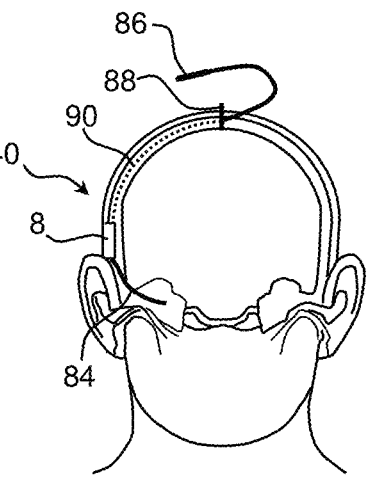
Fig. 7A  Fig. 7B  Fig. 7C
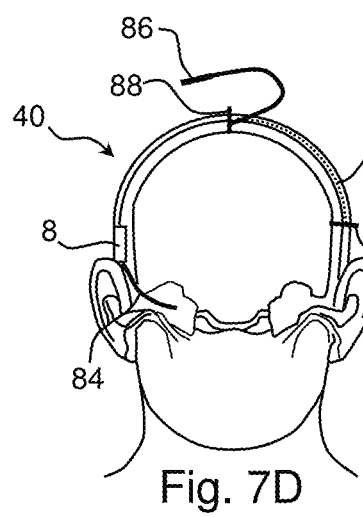
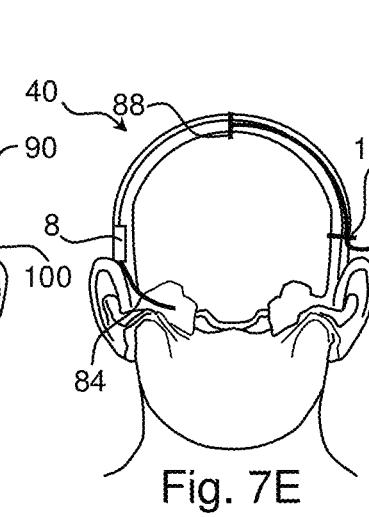
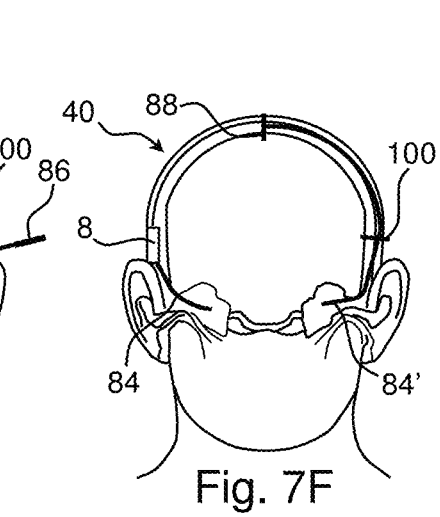
Fig. 7D  Fig. 7E  Fig. 7F

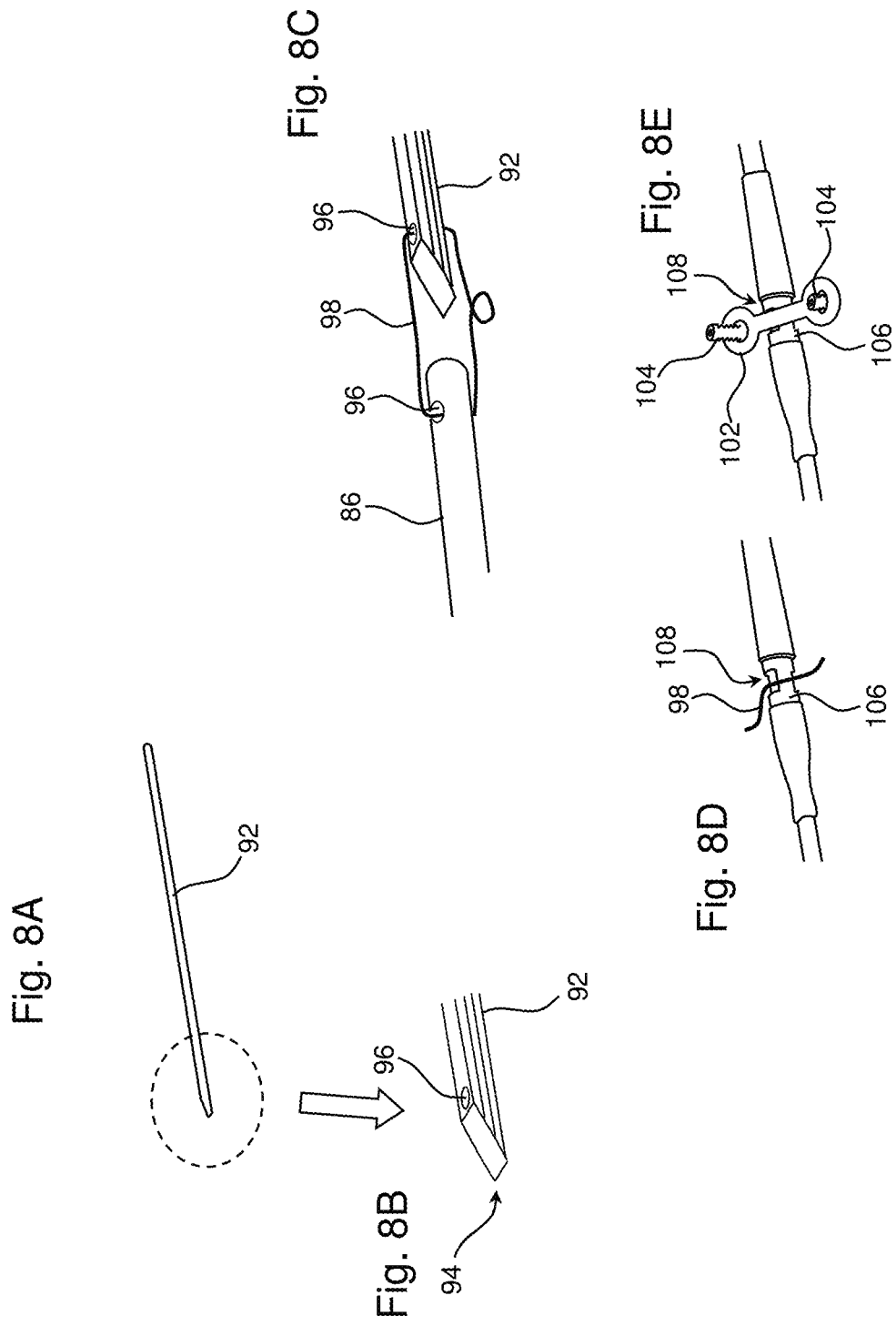

BINAURAL COCHLEAR IMPLANT SYSTEM

FIELD

The present disclosure relates to a binaural cochlear implant system comprising an implantable stimulator. More particularly, the disclosure relates to a binaural cochlear implant system using reinforcement of a contralateral lead of the binaural cochlear implant.

BACKGROUND

Among cochlear implant systems, the most commonly used device is a monaural cochlear implant configured to electrically stimulate an auditory nerve of a cochlea at one ear in order to generate hearing perception. As an alternative to the monaural cochlear implant, it is possible to use a binaural implant configured to provide the patient with a pseudo stereophony through simultaneous stimulation of cochleae at both ear using an ipsilateral electrode and a contralateral electrode.

As a binaural implant requires implanting two electrode arrays, a more complicated surgery is required than for implanting a classic monaural cochlear implant. During the surgery, the electrical wires to be placed into the lead during the tunneling of the electrode array can easily be damaged.

During the binaural implantation, there is a risk of rupturing electrical wires when the contralateral electrode array is pulled into the tunnel. There is also a risk of damaging the electrode array itself. In the prior art, a long silicone tubing covers and protects the electrode array and is maintained by friction silicone on silicone, but sometimes this tubing sticks on the lead and is difficult to remove.

It is desirable to be able to provide a binaural cochlear implant system that reduces or even eliminates the risk of damage on the electrical wires of the lead, during the tunneling of the electrode array so that the electrodes can be protected during the surgery.

It would also be desirable to provide a binaural cochlear implant system that requires a smaller size of tunnelling in order to reduce the time of healing of subjacent tissues. It may be further desirable to allow for reducing the number of steps required to pass the array. The present disclosure provides at least an alternative to the prior art.

SUMMARY

According to an aspect of the disclosure the binaural cochlear implant system comprises:
an implantable stimulator;
an ipsilateral cochlear implant electrode array connected to the stimulator and
a lead connected to the stimulator at a first end of the lead and provided with a contralateral binaural cochlear implant electrode array at a second end of the lead, the lead being configured to be implanted beneath the skin above the skull of a hearing aid user,
Wherein the lead comprises at least one electrical wire connecting the contralateral binaural cochlear implant electrode array with the stimulator, and a reinforcement fiber running along length of the at least one electrical wire.

Hereby it is possible to provide a binaural cochlear implant system that reduces or even eliminates the risk of damage on the electrical wires in the lead, during the tunneling of the electrode array. Accordingly, the electrodes can be protected during the surgery by using the binaural cochlear implant system according to the disclosure.

The binaural cochlear implant system comprises an implantable stimulator and the ipsilateral cochlear implant electrode array connected to the stimulator may have any suitable size and geometry.

The lead connected to the stimulator at a first end of the lead and being provided with a contralateral binaural cochlear implant electrode array at a second end of the lead may have any suitable length and thickness. However, since the lead is configured to be implanted beneath the skin above the skull of a hearing aid user, it is preferred that the thickness of the lead is as small as possible in order to minimize the size of the tunnelling in order to reduce the time of healing of subjacent tissues.

The lead comprises at least one electrical wire connecting the contralateral binaural cochlear implant electrode array with the stimulator, and a reinforcement fiber running along length of the at least one electrical wire.

The reinforcement fiber may be made of any suitable material and have any suitable thickness. The reinforcement fiber may be made in an implantable grade plastic such as Polyether ether ketone (PEEK), Poly(methyl methacrylate) (PMMA), Polyethylen (PE), and Aramid, however, the reinforcement fiber may alternatively be made in implantable metal such as grade stainless steel.

According to an embodiment of the disclosure, the reinforcement fiber is stronger than the at least one electrical wire. It may be beneficial that the reinforcement fiber has strength that is larger than the at least one electrical wire. It may be preferred that the reinforcement fiber has a tensile strength that is larger than the at least one electrical wire. This will provide reliability and ease during the passage through the skin.

According to another embodiment of the disclosure, the binaural cochlear implant system comprises a fixation member at the second end of the lead, the fixation member being configured to allow through passage of the contralateral binaural cochlear implant electrode array.

Hereby, it is possible to provide a permanent fixation of the reinforcing fiber on the stimulator and on the fixation member. The fixation may be provided by means of glue, crimping, melting, ultrasound or laser welding. It may be an advantage that an opening configured to provide access to the reinforcing fiber is provided on a side of the fixation member.

The fixation member may secure that when the lead reaches its maximum elongation, the reinforcing fiber is loaded and transfers the force to the fixation member.

The fixation member may be made of a rigid and hard implantable material such as an implantable grade plastic polyether ether ketone (PEEK) or polymethyl methacrylate (PMMA).

The fixation member may be shaped and configured to temporarily receive and firmly maintain a disposable protection structure of the contralateral electrode array during the packaging and storing, and especially during the surgery.

It may be an advantage that the at least one wire is fixedly attached to the fixation member.

It may be beneficial that the fixation member is arranged in such a manner that the stimulator is positioned on one side of the fixation member and the contralateral electrode array is positioned on an opposite side of the fixation member.

According to a further aspect of the disclosure, the fixation member is configured to fix a distance between the lead and the at least one electrical wire in accordance with the positioning of the lead and at least one wire at or within the fixation member.

According to another aspect of the disclosure during insertion of the contralateral binaural cochlear implant electrode array, further comprises a protection member, the protection member being configured to be removably attached to a distal end of the fixation member and to protectively surround the contralateral binaural cochlear implant electrode array. Hereby, the surgeon is able to handling the binaural cochlear implant system and touching the protection member in a manner that eliminates the risk of damaging the contralateral electrode array.

According to an even further aspect of the disclosure the protection member is disposable.

Hereby, the disposable protection protects the electrode array during packaging, storage and surgery and be thrown away after use.

According to another aspect of the disclosure the fixation member is configured to enable temporary fixation of the (disposable) protection member.

According to a further aspect of the disclosure the protection member is tube-shaped and configured to receive and contain an electrode array.

According to another aspect of the disclosure the protection member is configured to be fixed to the fixation member by means of suture. Additionally or alternatively, the protection member is configured to be fixed to the fixation member by means of a U-shaped clip configured to immovably press the protection member with respect to the fixation member. Apart from the disclosed means, it is apparent that other means may also be employed, wherein the means is configured to be removed such that the protection member and the fixation member may be detached from each other, typically immediately prior to insertion of contralateral electrode array into the cochlea.

According to a further aspect of the disclosure the protection member has a circular cross section.

According to another aspect of the disclosure, the protection member has an oval cross section.

Hereby the protection member can easily slide into the tunneling under the skin.

According to an even further aspect of the disclosure the protection member comprises a means such as a hole arranged at a distal end of the protection member and being configured to allow attaching a surgical tool, for example by using a suture, configured to facilitate passage of the contralateral binaural cochlear implant electrode array beneath the skin.

According to another aspect of the disclosure the arced proximal edge of the protection member comprises at section of a predetermined shape, such as a rectangular shape but preferably a spherical surface.

Hereby it is possible to attach the protection member to a surgical tool by a means such as a hole and preferably a suture. Accordingly, introduction of the protection member into the tunneling under the skin can be eased.

According to an even further aspect of the disclosure the surgical tool comprises attachment elements configured to attach the surgical tool to the protection member.

According to another aspect of the disclosure the wherein the surgical tool is provided with a sharp edge.

According to an even further aspect of the disclosure the surgical tool is provided with a flexible blade.

According to another aspect of the disclosure the lead comprises a multi-lumen tubing provided with a plurality of separated through-going canals configured to allow passage of the at least one electrical wire and the reinforcement fiber from the stimulator to at least to the fixation member.

According to another aspect of the disclosure the lead comprises a monolumen tubing provided with a through-going canal configured to allow passage of the at least one electrical wire and the reinforcement fiber from the stimulator to at least to the fixation member.

Hereby, it is possible to position the at least one electrical wire and the reinforcement fiber in separate canals in order to achieve predefined positions of the at least one electrical wire and the reinforcement fiber relative to each other.

According to a further aspect of the disclosure the reinforcement member and the at least one wire are positioned in separate through-going canals.

According to another aspect of the disclosure the relative distance between the reinforcement member and at least one wire is defined by relative positioning of the through-going canals.

According to an even further aspect of the disclosure the multi-lumen tubing has an oval cross section. According to an aspect, the multi-lumen tubing has a rectangular cross section. It is apparent that the multi-lumen tubing may include a different cross section such as circular.

Hereby it is possible to have two cylindrical through-going canals for wires and for a reinforcement fiber. Furthermore, it can be ensured that the traction force applied to the reinforcement fiber prevent the electrical wires (in order to make sure that the electric wire(s) will not be damaged).

According to an even further aspect of the disclosure the multi-lumen tubing has a circular cross section.

According to another aspect of the disclosure the multi-lumen tubing is provided with through-going canals having an oval cross section.

According to an even further aspect of the disclosure the multi-lumen tubing is provided with through-going canals having a circular cross section.

According to another aspect of the disclosure the multi-lumen tubing is provided with two or more through-going canals.

According to an even further aspect of the disclosure the multi-lumen tubing is provided with three or more through-going canals.

According to another aspect of the disclosure the multi-lumen tubing is provided with four or more through-going canals.

According to an even further aspect of the disclosure the reinforcement fiber has a uniform cross section. According to an aspect, the reinforcement fiber has a non-uniform cross section for example cross section area reducing from ipsilateral end to contralateral end. According to another aspect, the reinforcement fiber has a non-uniform cross section for example cross section area increasing from ipsilateral end to contralateral end. The non-uniform cross-section may be designed in order to withstand stress on the electrical wire/fiber during surgery and/or during use of the binaural CI device more effectively.

According to another aspect of the disclosure the reinforcement fiber has a circular cross section.

According to an even further aspect of the disclosure the reinforcement fiber has an oval cross section.

According to another aspect of the disclosure the reinforcement fiber has a basically rectangular cross section.

According to an even further aspect of the disclosure the reinforcement fiber comprises an implantable fabric.

According to another aspect of the disclosure the implantable fabric is a polyester mesh.

According to an even further aspect of the disclosure the reinforcement fiber comprises a sheath.

According to an aspect of the disclosure the sheath is a knitted sheath.

According to an even further aspect of the disclosure the sheath is a knitted sheath coextruded into a tubing.

According to an even further aspect of the disclosure the lead comprises the reinforcement fiber and a secondary reinforcement fiber arranged within the lead, wherein the secondary reinforcement fiber is arranged to run along the length of the reinforcement fiber and to extend beyond the fixation member. In a specific scenario including explantation of the contralateral electrode array, the secondary reinforcement fiber further provides additional strength and allows for avoiding potential breaking the electrical wires when the electrical wire along with the fiber is pulled out of the tunnel. In absence of (secondary) reinforcement fiber, such breakage would make explantation complicated because the broken part of the electrical wire retained within the skin would have to be extracted with a follow up surgery.

Hereby, the first reinforcement fiber can reinforce the lead allowing the required pull forces to be applied during the surgery and the secondary reinforcement fiber (arranged in the lead) can, when the lead has reached its maximum elongation, the second reinforcing fiber transfer force (e.g. to the fixation member).

According to another aspect of the disclosure the reinforcement fiber is stretchable along its length.

Hereby, it is possible to extend the reinforcement fiber. As the heads of children are growing. The use of a wire comprising a reinforcement fiber that is stretchable along its length allows for an already implanted binaural electrode to be stretched.

Hereby, the reliability solution can be increased.

According to a further aspect of the disclosure the reinforcement fiber comprises a stretchable mesh structure or stretchable knitted sheath.

According to another aspect of the disclosure the secondary reinforcement fiber comprises a stop member attached to a distal end of the secondary reinforcement fiber, the stop member being configured to cooperate with the fixation member in response to stretching of the reinforcement fiber.

Hereby, one can prevent the reinforcement fiber to completely slide out a fixation member.

According to an even further aspect of the disclosure the stop member is configured to restrict further stretching of the reinforcement fiber through cooperation between the stop member and fixation member once the reinforcement fiber has been stretched by a predefined allowable length.

According to another aspect of the disclosure the restriction of further traction of the secondary reinforcement fiber once the reinforcement fiber has been pulled into a predefined maximal allowable length configuration is achieved by bringing the protection member into contact with a portion of the fixation member.

Hereby, it is possible to provide a safe solution that prevents overstretching.

According to an even further aspect of the secondary reinforcement fiber is configured to transfer force to the fixation member when the lead has reached its maximum predefined allowable elongation.

According to another aspect of the disclosure the fixation member comprises an opening configured to provide access to the reinforcement fiber for allowing cutting the first reinforcement fiber when the reinforcement fiber has been stretched by the predefined allowable length.

Hereby, cutting the first reinforcement fiber is eased.

According to an even further aspect of the disclosure a protective layer at least partly surrounds the electrical wire (s). Such protective layer may comprise a silicone tubing.

The protective layer secures that direct contact between the hard fixation member and the fragile electric wire(s) can be avoided.

According to another aspect of the disclosure the protective layer is made in a soft material.

According to an even further aspect of the disclosure the fixation member comprises a receiving section configured to receive an attachment structure that is configured to immovably attach the fixation member to skull bone of the user.

Hereby, the attachment of the attachment structure can be eased. It is furthermore possible to stabilize the inserted contralateral electrode array.

According to another aspect of the disclosure the attachment structure is selected from a group consisting of a suture that is configured to affix with the skull bone and a strip comprising at least two holes configured to receive implantable screw that is fixable to skull bone of the user.

According to an even further aspect of the disclosure the protection member comprises:
- a lumen adapted to at least partially receive the fixation member and completely receive the contralateral binaural cochlear implant electrode array and
- a groove adapted to receive a suture, wherein the suture is adapted to provide attachment between the protection to the fixation member.

Hereby, it is possible to provide a user-friendly and reliable solution.

According to another aspect of the disclosure the kit is a kit comprising a binaural cochlear implant system according to the disclosure and one or more of the following: protection member, suture, surgical tool, implantable screws, attachment structure.

Such kit makes it possible to reduce even eliminates the risk of damage on the electrical wires in the lead, during the tunneling of the electrode array so that the electrodes can be protected during the surgery. Furthermore, the kit enables the surgeon to minimize the size of tunnelling, whereby the time of healing of subjacent tissues can be reduced.

According to another aspect of the disclosure the method for implanting a binaural cochlear implant system comprises the following steps:
- positioning a stimulator in the mastoid bone;
- inserting an ipsilateral electrode array;
- performing a vertex incision and a tunnelling by means of a surgical tool; and
- inserting a contra-lateral electrode array This surgical tool may be a flexible tool comprising a flexible blade.

It may be an advantage that a sharp edge is provided on its proximal side. Hereby, it is possible to lift off the fascia from the periosteum.

According to another aspect of the disclosure the method for implanting a binaural cochlear implant system comprises the following step:
- attaching a disposable protection to the surgical tool, prior to removing the flexible tool and after a tunnelling from the vertex incision to the ipsilateral side is provided.

According to a further aspect of the disclosure the method for implanting a binaural cochlear implant system comprises the following step:
- pulling off the surgical tool from the tunnelling until the lead has been taken out in vertex position.

According to an even further aspect of the disclosure the method for implanting a binaural cochlear implant system comprises the following step:
    performing a contralateral incision;
    performing a tunnelling from the controlateral side to the vertex incision by means of the surgical tool.

According to another aspect of the disclosure the method for implanting a binaural cochlear implant system comprises the following step:
    performing a contralateral incision;
    performing a tunnelling from the controlateral side to the vertex incision by means of the surgical tool.

According to an even further aspect of the disclosure the method for implanting a binaural cochlear implant system comprises the following step:
    attaching the disposable protection to the surgical tool;
    pulling the surgical tool back and taking off the lead in the controlateral position.

According to another aspect of the disclosure the method for implanting a binaural cochlear implant system comprises the following step:
    closing the vertex incision.

According to an even further aspect of the disclosure the method for implanting a binaural cochlear implant system comprises the following step:
    removing the disposable protection.

This may be done by cutting and removing a non-absorbable suture or the U-shaped pin. It is apparent to the skilled person that other means used to fix the protection member with the fixation member may now be removed in order to achieve this step.

According to another aspect of the disclosure the method for implanting a binaural cochlear implant system comprises the following step:
    while having access to the fixation member fixing the fixation member with either a suture attached to the bone or a jump and one or more implantable screws.

According to an even further aspect of the disclosure the method for implanting a binaural cochlear implant system comprises the following step:
    insertion of a controlateral electrode array into the cochlea.

According to another aspect of the disclosure the method for implanting a binaural cochlear implant system comprises the following step:
    closing the controlateral incision.

BRIEF DESCRIPTION OF DRAWINGS

The aspects of the disclosure may be best understood from the following detailed description taken in conjunction with the accompanying figures. The figures are schematic and simplified for clarity, and they just show details to improve the understanding of the claims, while other details are left out. Throughout, the same reference numerals are used for identical or corresponding parts. The individual features of each aspect may each be combined with any or all features of the other aspects. These and other aspects, features and/or technical effect will be apparent from and elucidated with reference to the illustrations described hereinafter in which:

FIG. 2A shows a schematic view of a prior art a binaural cochlear implant;

FIG. 2B shows a schematic view of a prior art a binaural cochlear implant;

FIG. 2C shows a schematic view of a prior art tool applied to provide a hollow path;

FIG. 2D shows a schematic view of a prior art procedure, in which the contra-lateral electrode being inserted into the hollow path shown in FIG. 2C;

FIG. 2E shows a schematic view of the contralateral electrode inserted into the hollow path shown in FIG. 2C;

FIG. 6A shows a schematic, cross sectional view of a lead according to an embodiment of the disclosure;

FIG. 6B shows a schematic, cross sectional view of the lead shown in FIG. 6A, in a first configuration;

FIG. 6C shows another schematic, cross sectional view of the lead shown in FIG. 6A, in a second configuration;

FIG. 6D shows a schematic view of a binaural cochlear implant system according to an embodiment of the disclosure;

FIG. 6E shows a close-up view of the fixation member of the binaural cochlear implant system shown in FIG. 6D in a first configuration;

FIG. 6F shows a close-up view of the fixation member of the binaural cochlear implant system shown in FIG. 6D in a second configuration;

FIG. 6G shows a close-up view of an electrical wire of a binaural cochlear implant system according to the invention in a first un-stretched configuration;

FIG. 6H shows a close-up view of an electrical wire of a binaural cochlear implant system according to the disclosure in a second stretched configuration;

FIG. 7A shows a schematic view of a first step of a method for implanting a binaural cochlear implant system according to the disclosure;

FIG. 7B shows a schematic view of a second step of the method for implanting a binaural cochlear implant system according to the disclosure;

FIG. 7C shows a schematic view of a third step of the method for implanting a binaural cochlear implant system according to the disclosure;

FIG. 7D shows a schematic view of a fourth step of the method for implanting a binaural cochlear implant system according to the disclosure;

FIG. 7E shows a schematic view of a sixth step of the method for implanting a binaural cochlear implant system according to the disclosure;

FIG. 7F shows a schematic view of a seventh step of the method for implanting a binaural cochlear implant system according to the disclosure;

FIG. 8A shows a schematic view of a tool according to the disclosure;

FIG. 8B shows a close-up view of the distal portion of the tool shown in FIG. 8A;

FIG. 8C shows a schematic view of the tool shown in FIG. 8A attached to a disposable protection member;

FIG. 8D shows a schematic view of a fixation member being attached to a bone by means of suture and FIG. 8E shows a schematic view of a fixation member being attached to a bone by means of a jump and two implantable screws.

DETAILED DESCRIPTION

Figure 1A:
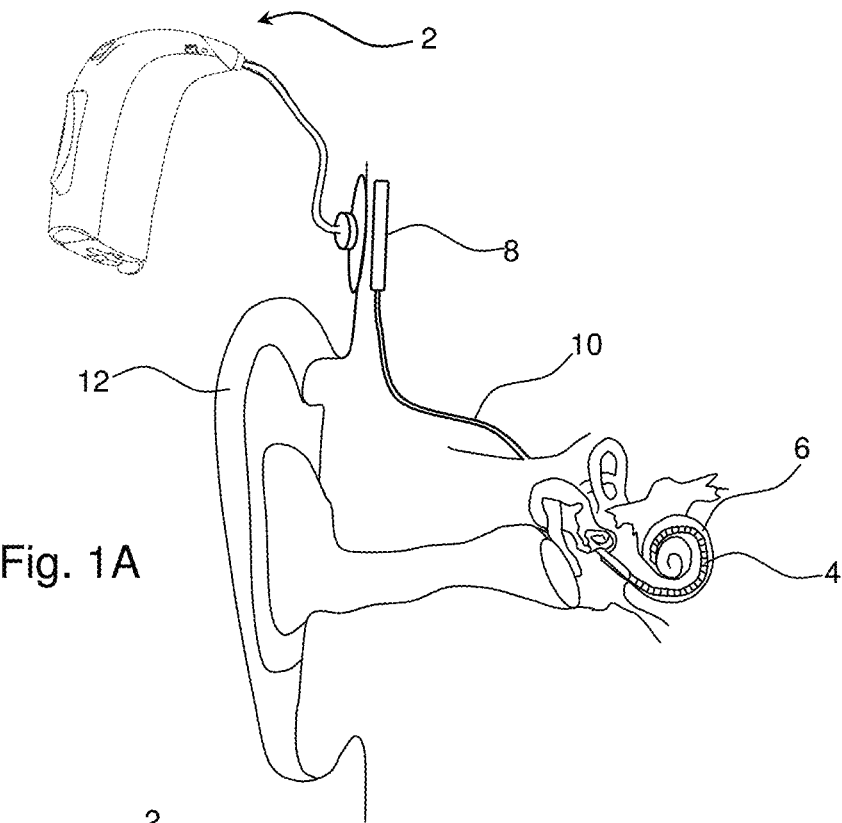
FIG. 1A shows a schematic view of a prior art cochlear implant including the external and implanted parts.

The detailed description set forth below in connection with the appended drawings is intended as a description of various configurations. The detailed description includes specific details for the purpose of providing a thorough understanding of various concepts. However, it will be apparent to those skilled in the art that these concepts may be practiced without these specific details.

A hearing device may include a hearing aid that is adapted to improve or augment the hearing capability of a user by receiving an acoustic signal from a user's surroundings, generating a corresponding audio signal, possibly modifying the audio signal and providing the possibly modified audio signal as an audible signal to at least one of the user's ears. Such audible signals is provided in the form of electric signals transferred directly or indirectly to cochlear nerve.

The hearing device is adapted to be worn in any known way. This may include arranging a unit of the hearing device as an entirely or partly implanted unit such as in Cochlear Implant.

A "hearing system" refers to a system comprising one or two hearing devices, and a "binaural hearing system" refers to a system comprising two hearing devices where the devices are adapted to cooperatively provide audible signals to both of the user's ears. The hearing system or binaural hearing system may further include auxiliary device(s) that communicates with at least one hearing device, the auxiliary device affecting the operation of the hearing devices and/or benefitting from the functioning of the hearing devices. A wired or wireless communication link between the at least one hearing device and the auxiliary device is established that allows for exchanging information (e.g. control and status signals, possibly audio signals) between the at least one hearing device and the auxiliary device. Such auxiliary devices may include at least one of remote controls, remote microphones, audio gateway devices, mobile phones, public-address systems, car audio systems or music players or a combination thereof. The audio gateway is adapted to receive a multitude of audio signals such as from an entertainment device like a TV or a music player, a telephone apparatus like a mobile telephone or a computer, a PC. The audio gateway is further adapted to select and/or combine an appropriate one of the received audio signals (or combination of signals) for transmission to the at least one hearing device. The remote control is adapted to control functionality and operation of the at least one hearing devices. The function of the remote control may be implemented in a SmartPhone or other electronic device, the SmartPhone/ electronic device possibly running an application that controls functionality of the at least one hearing device.

In general, a hearing device includes i) an input unit such as a microphone for receiving an acoustic signal from a user's surroundings and providing a corresponding input audio signal, and/or ii) a receiving unit for electronically receiving an input audio signal. The hearing device further includes a signal processing unit for processing the input audio signal and an output unit for providing an audible signal to the user in dependence on the processed audio signal.

The input unit may include multiple input microphones, e.g. for providing direction-dependent audio signal processing. Such directional microphone system is adapted to enhance a target acoustic source among a multitude of acoustic sources in the user's environment. In one aspect, the directional system is adapted to detect (such as adaptively detect) from which direction a particular part of the microphone signal originates. This may be achieved by using conventionally known methods. The signal processing unit may include amplifier that is adapted to apply a frequency dependent gain to the input audio signal. The signal processing unit may further be adapted to provide other relevant functionality such as compression, noise reduction, etc. The output unit may include an output transducer such as one or more output electrodes for providing the electric signals such as in a cochlear implant.

Now referring to FIG. 1A, which illustrates a prior art cochlear implant including an external device (a hearing aid) 2 coupled to an electromagnetic coupling arranged on the skin of a hearing aid user close to an implanted stimulator 8. A lead 10 is electrically connected to the implanted stimulator 8 and to an electrode 4 inserted into the cochlea 6 for electrically stimulate the auditory nerve in order to produce hearing sensation.

Figure 1B:
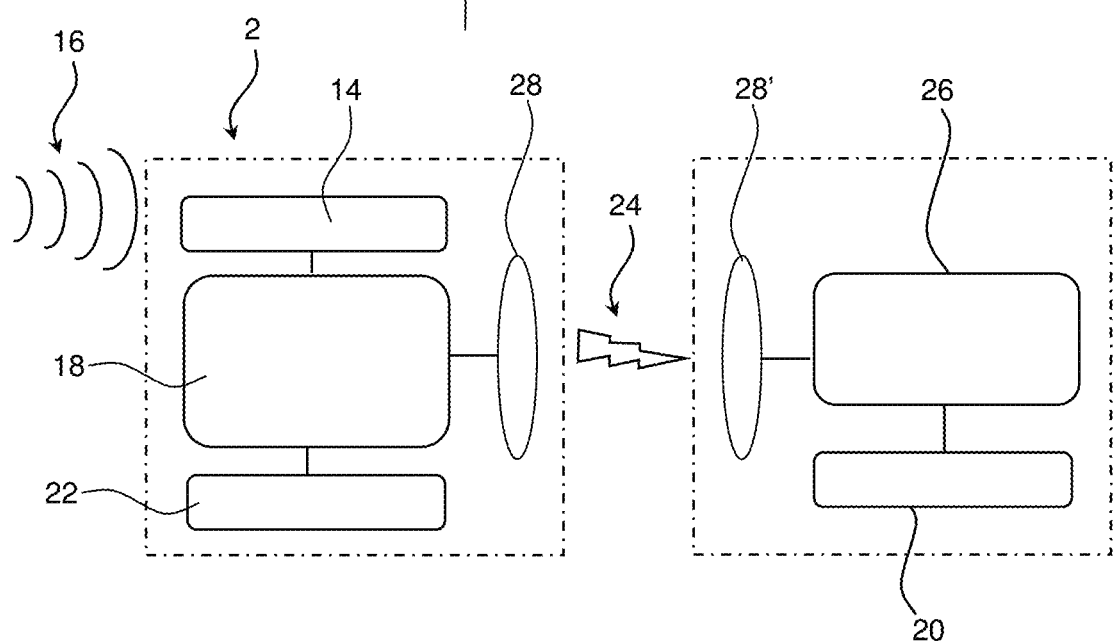
FIG. 1B shows a schematic view of the principle of functioning of a prior art cochlear implant.

FIG. 1B illustrates a schematic view of the principle of functioning of a prior art cochlear implant. The external device 2 is a hearing aid 2 comprising a battery 22 and a microphone 14 electrically connected to a signal processor 18 that is electrically connected to a coil 28 configured to wirelessly communicate (electromagnetic coupling 24) with the implanted stimulator comprising a coil 28' electrically connected to an electrode array 20 via stimulation electronics 26.

The stimulation electronics 26 transforms information received from the external device 2 into electrical signals that are sent via the electrode array 20 to electrically stimulate the auditory nerve of the hearing aid user.

FIG. 2A illustrates a schematic view of a prior art binaural cochlear implant 30 comprising an implantable stimulator 8 and a first electrode array 20 and a second electrode array 20' electrically connected to the implantable stimulator 8.

FIG. 2B illustrates a schematic view of a prior art binaural cochlear implant implanted in a hearing aid user 40 having outer ears 12, 12'. A first electrode array is arranged in the ipsilateral side 32 and a second electrode array is arranged in the controlateral side 34. The first step of the surgery is similar to the one performed when implanting a classic monaural cochlear implant. The first step takes place in the ipsilateral side 32 and includes: ipsilateral incision; mastoidectomy; placement of the stimulator; cochleostomy and insertion of the electrode array.

During a prior art binaural surgery additional steps are performed. A tunneling 90 from ipsilateral side 32 to the cortex is made. A contralateral electrode tunneling 90' is made and an incision at vertex 36 is created. When the controlateral electrode has been inserted through this first tunnel 90 the ipsilateral side 32 is closed.

When the ipsilateral implantation has been done, the ipsilateral incision has been closed and the hearing aid user 40 can be moved on the surgical table so that the controlateral side 34 faces the surgeon.

A controlateral incision is made in the controlateral side 34 and a tunneling 90' from vertex to controlateral side 34 is provided in order to insert the controlateral electrode through this tunnel 90'. Hereafter the incision at vertex 36 is closed.

The finishing operations take place on the controlateral side 34 and correspond to the ones carried out in a classic implantation. These operation steps include: mastoidectomy; cochleostomy; insertion of the controlateral electrode array and eventually the closing of the controlateral implantation site 34.

FIG. 2C illustrates a schematic view of a prior art tool 42 applied to provide a hollow path 38 (a canal/tunnelling in the skin). The tool 42 comprises an enlarged distal portion configured to create a hollow path 38 by moving the tool 42 in the direction 46 indicated by the arrow.

FIG. 2D illustrates a schematic view of a prior art procedure, in which the contralateral electrode array 20 of a prior art binaural cochlear implant system 30 arranged in a tube 44 is being inserted into the hollow path 38 shown in FIG. 2C. The contralateral electrode array 20 is electrically connected to an implantable stimulator 8 that is further electrically connected to a second electrode array 20'. The tube 44 is being inserted by moving the tube in the direction 46 indicated by a direction arrow 46.

FIG. 2E illustrates a schematic view of the contralateral electrode array 20 that has been inserted into the hollow path 38 shown in FIG. 2D. The tube shown in FIG. 2D has been removed.

Figure 3A:
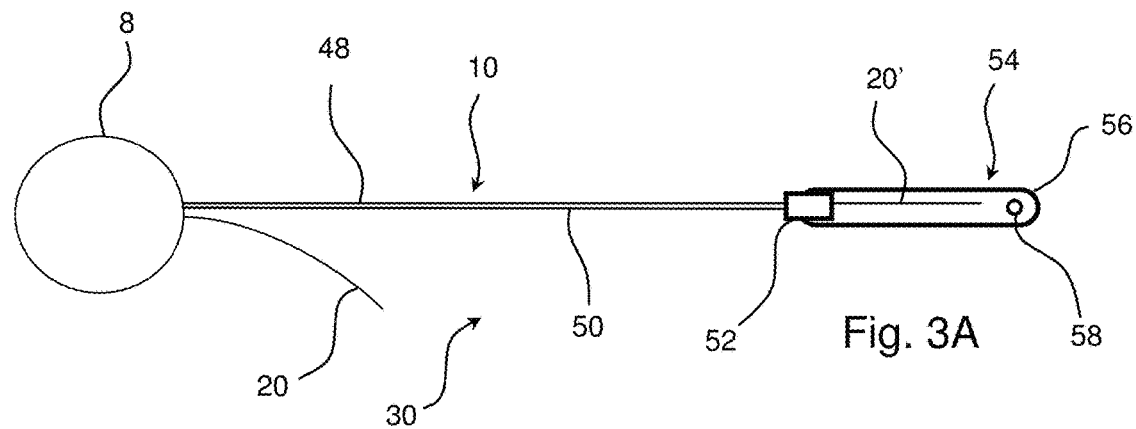
FIG. 3A shows a schematic view of a binaural cochlear implant system according to an embodiment of the disclosure.

FIG. 3A illustrates a schematic view of a binaural cochlear implant system 30 according to an embodiment of the disclosure. The binaural cochlear implant system 30 comprises an implantable stimulator 8 electrically connected to a first, ipsilateral electrode array 20 and a second, controlateral electrode array 20'. The binaural cochlear implant system 30 comprises a lead 10 comprising an electrical connection between the stimulator 8 and the controlateral electrode array 20'. The implantable stimulator 8 contains electronics and a coil (as explained with reference to FIG. 1B). In the proximal end 56 of the protection member 54 a hole 58 may be provided.

A reinforcement fiber 50 extends parallel to/along the electrical wires 48 of the lead 10. The reinforcing fiber 50 may be made of any suitable implantable material such as PEEK, PMMA, PE, aramid, metal (e.g. implantable grade stainless steel) or combinations thereof. The reinforcement fiber 50 is attached to the stimulator 8 and on a fixation member 52 provided at the proximal end of a protection member 54.

The reinforcement fiber 50 may be attached to the stimulator 8 and to the fixation member 52 by any suitable attachment means. The reinforcement fiber 50 may be glued, crimped, melted, ultrasound fixed or laser welded to the stimulator 8 and to the fixation member 52. The fixation member 52 may be made of a rigid and hard implantable material such as an implantable grade plastic PEEK, PMMA.

The electrical wires 48 extend through the fixation member 52 and therefore the electrical wires 48 are protected from handling during surgery. The fixation member 52 is configured to temporarily receive and firmly maintain a disposable protection member 54 of the controlateral electrode array 20' during packaging, storing and surgery.

Actually, the surgeon will be able to handle the binaural cochlear implant system 30 and thus touch the disposable protection member 54 without risking damage of the controlateral electrode array 20'. When the binaural cochlear implant system 30 has been implanted, the surgeon will be able to remove the disposable protection member 54 and finish the surgery. The disposable protection member 54 typically includes a spherical proximal end 56 in order to ease insertion into a tunneling under the skin. A hole 213 allows to the surgeon to put a suture in order to help the introduction of the device into the tunneling performed under the skin.

Figure 3B:
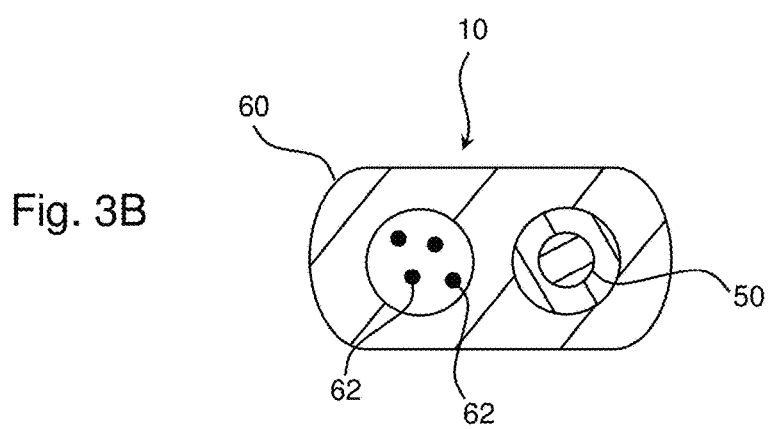
FIG. 3B shows a schematic, cross sectional view of a lead according to an embodiment of the disclosure.
Figure 3C:
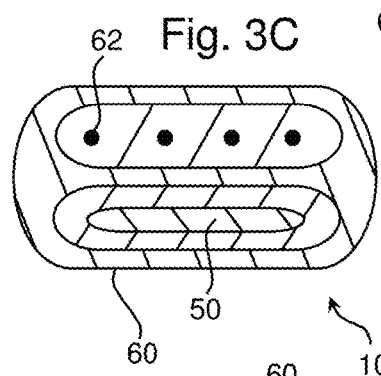
FIG. 3C shows a schematic, cross sectional view of a lead according to another embodiment of the disclosure.
Figure 3D:
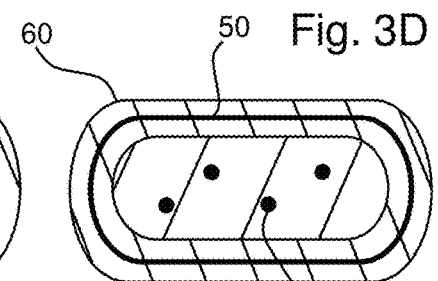
FIG. 3D shows a schematic, cross sectional view of a lead according to a further embodiment of the disclosure.
Figure 3E:
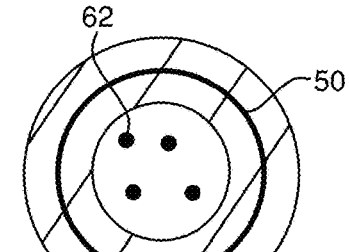
FIG. 3E shows a schematic, cross sectional view of a lead according to another embodiment of the disclosure.
Figure 3F:
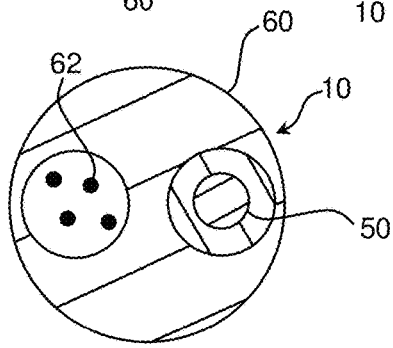
FIG. 3F shows a schematic, cross sectional view of a lead according to an even further embodiment of the disclosure.
Figure 3G:
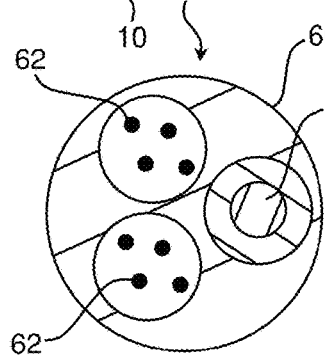
FIG. 3G shows a schematic, cross sectional view of a lead according to a further embodiment of the disclosure.
Figure 3H:
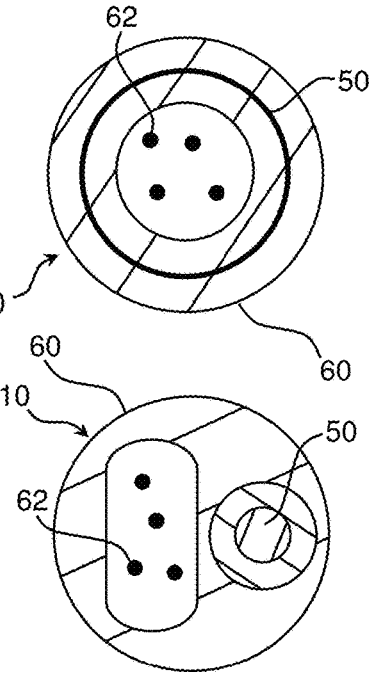
FIG. 3H shows a schematic, cross sectional view of a lead according to another embodiment of the disclosure.

FIG. 3B illustrates a schematic, cross sectional view of a lead 10 according to an embodiment of the disclosure. The lead 10 comprises a multi-lumen tubing 60 with an oval cross section in order to have two inner cylindrical paths respectively to allow the placement of electrical wires 62 and a reinforcement fiber 50.

The lead 10 is provided with two separate holes. Hereby, it is possible to separate the electrical wires 62 and the reinforcement fiber 50. Accordingly, tensile forces applied on the strong reinforcement fiber 50 will not damage the fragile electrical wires 62. Even though micro movements can be expected on the lead 10, they will not provoke frictions and wear of the insulation of the electrical wires 62.

FIG. 3C to FIG. 3H illustrate schematic, cross sectional views of leads 10 according to different embodiments of the disclosure. The lead 10 can be arranged in a multi-lumen tubing 60 having a cylindrical or oval cross section. The multi-lumen tubing 60 may have different numbers of holes (canals) of various geometry including cylindrical and oval cross sections. The multi-lumen tubing 60 is provided with a reinforcement fiber 50. The reinforcement fiber 50 may be round/arced, flat, circular or oval or any combinations thereof and may be made in any suitable material including an implantable fabric such as polyester mesh or be made as a knitted sheath, e.g. a knitted sheath that is coextruded directly into the multi-lumen tubing 60.

Figure 4A:
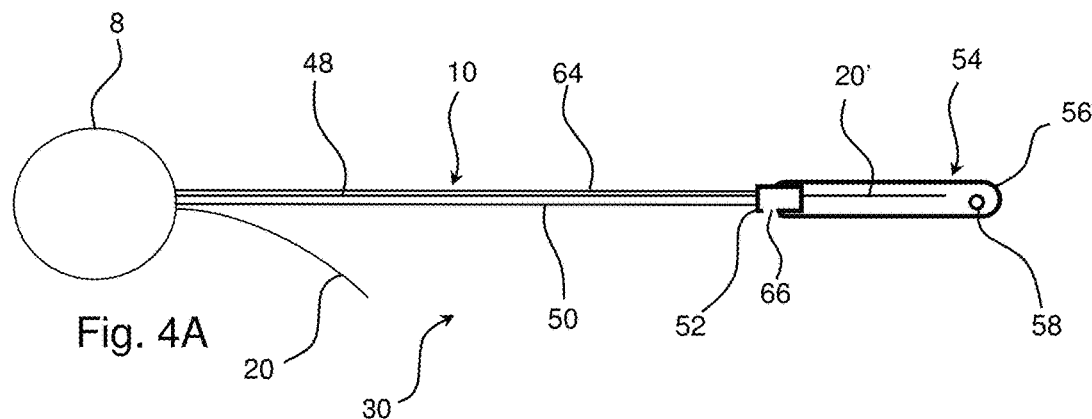
FIG. 4A shows a schematic view of a binaural cochlear implant system according to an embodiment of the disclosure.
Figure 4B:
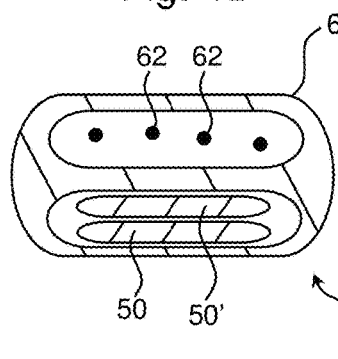
FIG. 4B shows a schematic, cross sectional view of a lead according to an embodiment of the disclosure.
Figure 4C:
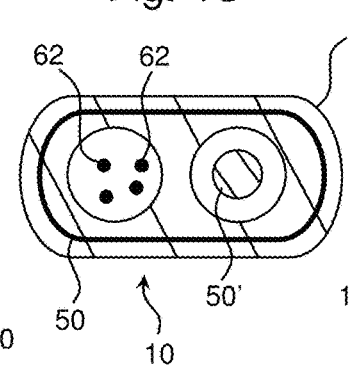
FIG. 4C shows a schematic, cross sectional view of a lead according to another embodiment of the disclosure.
Figure 4D:
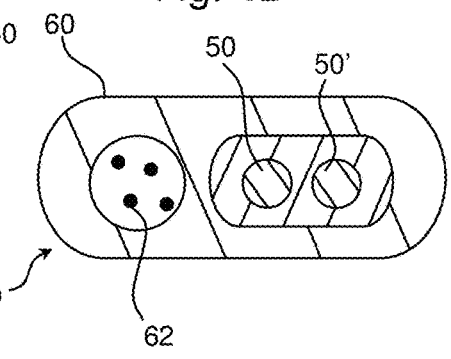
FIG. 4D shows a schematic, cross sectional view of a lead according to a further embodiment of the disclosure.
Figure 4E:
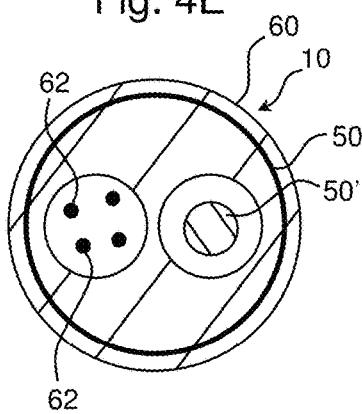
FIG. 4E shows a schematic, cross sectional view of a lead according to another embodiment of the disclosure.
Figure 4F:
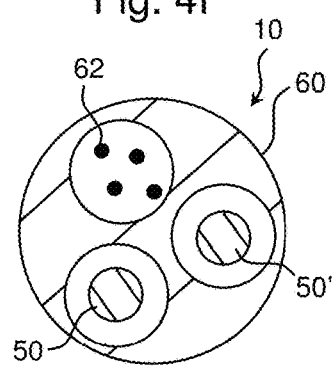
FIG. 4F shows a schematic, cross sectional view of a lead according to an even further embodiment of the disclosure.
Figure 4G:
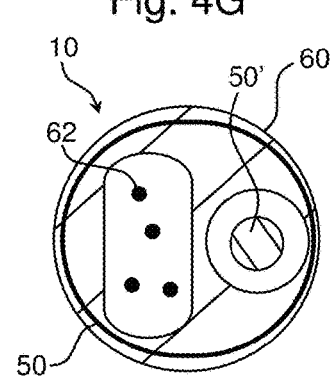
FIG. 4G shows a schematic, cross sectional view of a lead according to a further embodiment of the disclosure.

FIG. 4A illustrates a schematic view of a binaural cochlear implant system 30 according to an embodiment of the disclosure. The binaural cochlear implant system 30 basically corresponding to the binaural cochlear implant system shown in FIG. 3A, however, an opening 66 is provided in the fixation member 52. The fixation member 52 may be made of any suitable material e.g. a rigid and hard implantable material such as an implantable grade plastic PEEK, PMMA.

FIG. 4B to FIG. 4G illustrate schematic, cross sectional views of leads 10 according to different embodiments of the disclosure. It can be seen that the lead 10 can be arranged in a multi-lumen tubing 60 having a cylindrical or oval cross section. The multi-lumen tubing 60 may have different numbers of holes (canals) of various geometry including cylindrical and oval cross sections. Each multi-lumen tubing 60 is provided with a first reinforcement fiber 50 and a secondary reinforcement fiber 50'. The reinforcement fibers 50, 50' may be round/arced, flat, circular or oval and may be made in any suitable material including an implantable fabric such as polyester mesh or be made as a knitted sheath, e.g. a knitted sheath that is coextruded directly into the multi-lumen tubing 60.

Figure 5A:
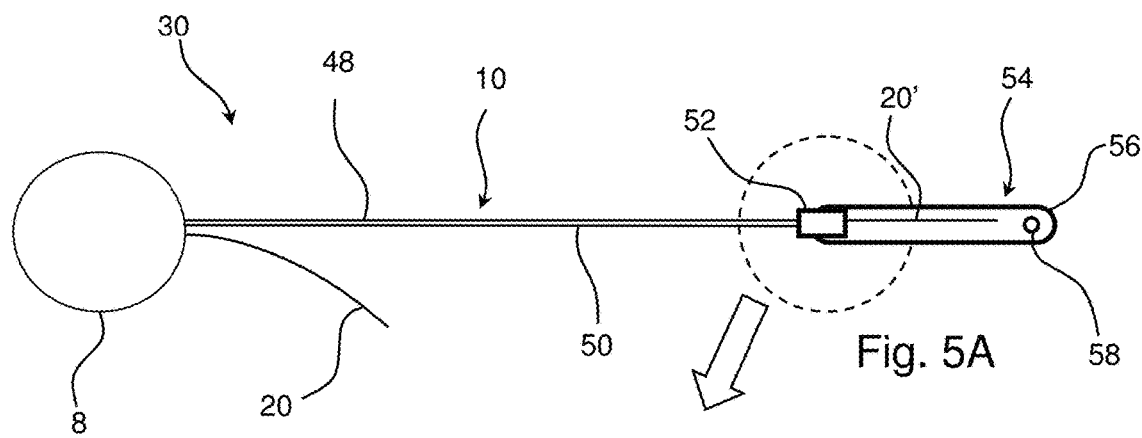
FIG. 5A shows a schematic view of a binaural cochlear implant system according to an embodiment of the disclosure.

FIG. 5A illustrates a schematic view of a binaural cochlear implant system 30 according to an embodiment of the disclosure. The binaural cochlear implant system 30 basically corresponding to the binaural cochlear implant system shown in FIG. 3A.

Figure 5B:
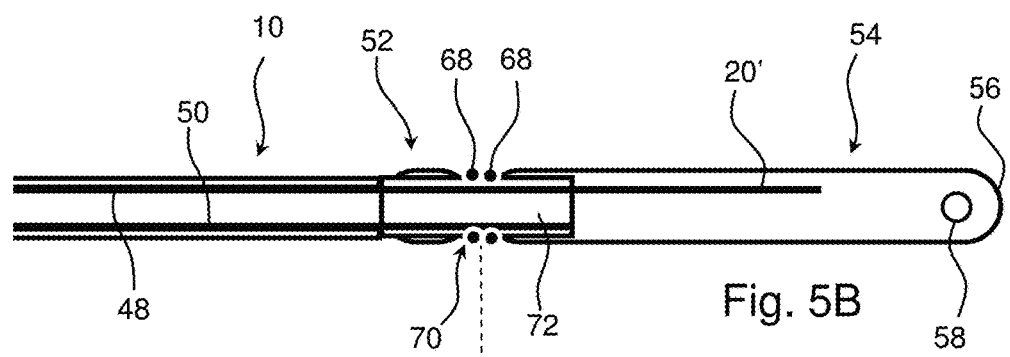
FIG. 5B shows a schematic, close-up view of the view of a fixation member of the binaural cochlear implant system shown in FIG. 5A.

FIG. 5B illustrates a schematic, close-up view of the view of a fixation member 52 of the binaural cochlear implant system 30 shown in FIG. 5A. The lead 10 comprises a reinforcement fiber 50 extending parallel to electrical wires 48 extending along the length of the lead 10. The reinforcement fiber 50 is attached to a fixation member 52. The electrical wires 48 extend through the fixation member 52 into a hollow protection member 54 provided with a hole 58 in its proximal end 56. The electrical wires 48 is surrounded by a protective layer 72, preferably made of a soft material. The protective layer 72 prevents direct contact between the hard fixation member 52 and the more fragile electrical wires 48. A groove 70 is provided in the fixation member 52 and fixing structure 68 is attached in the groove 70.

The disposable protection member 52 is tubular and the controlateral electrode array 20' may be inserted during the manufacturing process. The disposable protection member 52 is attached to the fixation member 52 by means of two turns of a non-absorbable suture 68. Two opposite grooves 70 are provided in the disposable protection member 52 in order to allow the suture 68 to be attached in the grooves 70.

Figure 5C:
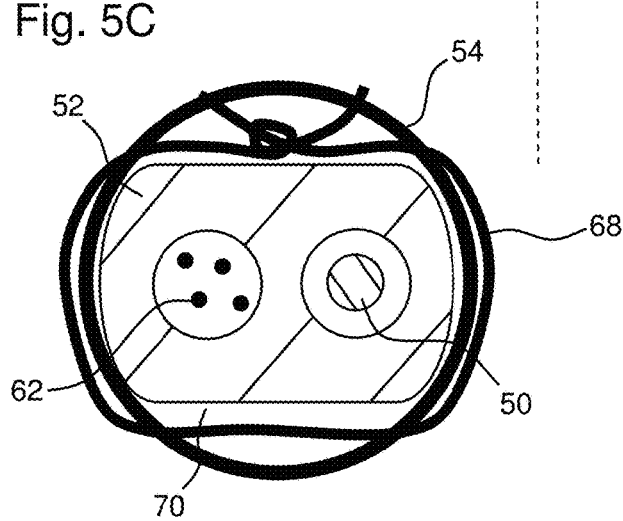
FIG. 5C shows a schematic, cross-sectional view of the fixation member shown in FIG. 5B.

FIG. 5C illustrates a schematic, cross-sectional view of the fixation member 52 shown in FIG. 5B. It can be seen that the fixation member 52 has an oval cross section and that electric wires 62 are arranged in a first canal, whereas a reinforcement fiber 50 is provided in another canal arranged in a non-zero distance from the first canal. The protection member 54 and the fixing structure 68 explained with reference to FIG. 5B are illustrated in FIG. 5C.

Figure 5D:
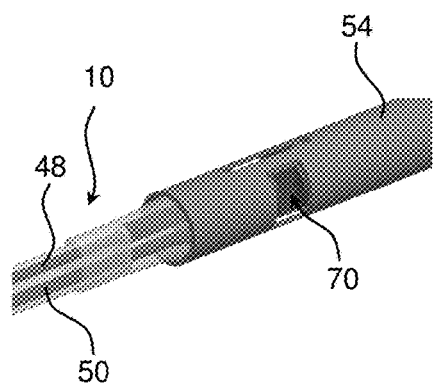
FIG. 5D shows a schematic, perspective view of a part of the binaural cochlear implant system shown in FIG. 5A.
Figure 5E:
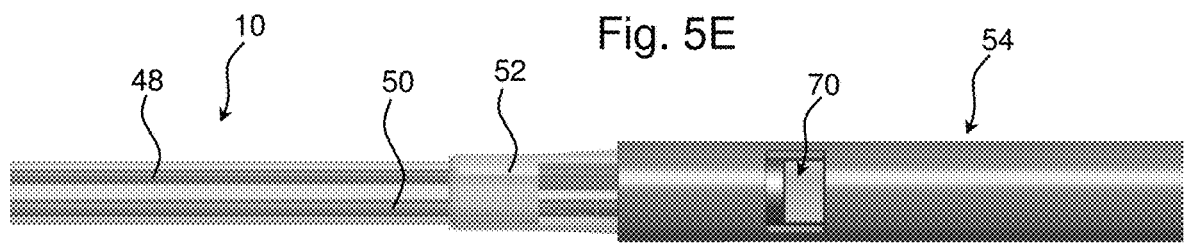
FIG. 5E shows a schematic, side view of the binaural cochlear implant system shown in FIG. 5D.

FIG. 5D illustrates a schematic, perspective view of a part of the binaural cochlear implant system shown in FIG. 5A. and FIG. 5E illustrates a schematic, side view of the binaural cochlear implant system shown in FIG. 5D. It can be seen that the lead 10 comprises wires 48 arranged in a first canal spaced from a reinforcement fiber 50. The binaural cochlear implant system comprises a protection member 54 provided with openings (grooves) 70 and a fixation member 52 is provided close to the proximal end of the protection member 54.

FIG. 6A illustrates a schematic, cross sectional view of a lead 10 according to an embodiment of the disclosure. The lead 10 has a basically oval cross section. A first reinforcement fiber 50 extends parallel to the periphery of the outer surface of the lead 10 and a secondary reinforcement fiber 50' is provided in a first canal in the lead. Electrical wires 62 extend in a second canal provided in the lead 10.

FIG. 6B illustrates a schematic, cross sectional view of the lead 10 shown in FIG. 6A, in a first configuration, in which a reinforcement fiber provided as a knitted sheath 74 is in an initial (un-stretched) state. The meshes 76 are relative small.

FIG. 6C illustrates a schematic, cross sectional view of the lead 10 shown in FIG. 6A, in a second configuration, in which the lead 10 is completely stretched and the meshes 76 of the knitted sheath 74 have reached their maximum dimensions.

FIG. 6D illustrates a schematic view of a binaural cochlear implant system 30 according to an embodiment of the disclosure. The binaural cochlear implant system 30 comprises an implantable stimulator 8, an ipsilateral electrode array 20 and a contralateral electrode array 20' as well as a fixation member 52.

FIG. 6E illustrates a close-up view of the fixation member 52 of the binaural cochlear implant system shown in FIG. 6D in a first configuration. The binaural cochlear implant system comprises a multi-lumen tubing 60 provided with three canals, in which electrical wires 48, a first reinforcement fiber 50 and a secondary reinforcement fiber 50' extend through.

A fixation member 52 made of a rigid and hard implantable material is provided at the proximal end of the first reinforcement fiber 50. The first reinforcement fiber 50 is attached to the fixation member 52. It may be glued, crimped, melted, ultra-sound fixed or laser welded. The electrical wires 48 extend through another canal displaced from the other canals. The electrical wires 48 are surrounded by a protective layer made of a soft material in order to avoid direct contact between the hard fixation member 52 and the electrical wires 48.

An opening 80 is provided in the fixation member 52. The opening 80 is large enough to allow a scalpel blade to cut the first reinforcement fiber 50. In this manner, the electrical wires 48 and the secondary reinforcement fiber 50' can be protected from misused.

The secondary reinforcement fiber 50' extends through a third canal of the fixation member 52. A gap between the fiber and the cans allows the fixation member 52 to slide along the length of the secondary reinforcement fiber 50'. At its proximal extremity, the secondary reinforcement fiber 50' is provided with a stop member 78 configured and arranged to prevent the secondary reinforcement fiber 50' from sliding out the fixation member 52. Depending of the distance D between the stop member 78 and the fixation member 52 in its initial state and when the first reinforcement fiber 50 has been cut, the lead 10 will be able to be stretched to a degree corresponding to this distance D, until the stop member 78 will be brought into contact with the fixation member 52.

FIG. 6F illustrates a close-up view of the fixation member 52 of the binaural cochlear implant system shown in FIG. 6D in a second configuration. In the shown "released state" view, the first reinforcement fiber 50 has been cut by the surgeon through the opening 80. A traction force has been applied to the lead 10 by using the fixation member 52. Accordingly, the lead 10 has been stretched.

Consequently, the soft material of the multi-lumen tubing has been stretched. The first reinforcement fiber 50, however, has maintained its length. Therefore, there is a gap between the opening 80 and the middle extremity of the first reinforcement fiber 50. At the same time, the fixation member 52 slides along the length of the second reinforcement fiber 50'. Accordingly, the stop member 78 of the second reinforcement member 50' reaches the fixation member 52. Therefore, the relative movement is restricted and the tensile forces are transferred to the lead 10.

The electrical wires 48 need to be capable of being extended without breaking due to the stress of the elongation of the lead 10. Accordingly, it is preferred that the electrical wires 48 are spring-shaped or coil-shaped.

FIG. 6G illustrates a close-up view of an electrical wire 48 of a binaural cochlear implant system according to the invention in a first unstretched configuration, whereas FIG. 6H illustrates a close-up view of the electrical wire 48 shown in FIG. 6G in a second stretched configuration.

FIG. 7A illustrates a schematic view of a first step of a method for implanting a binaural cochlear implant system according to the disclosure. The surgeon has already arranged the stimulator 8 on the mastoid bone and inserted the ipsilateral electrode array 84. The controlateral electrode array and the disposable assembly surrounding its distal end are shown next the head of the hearing aid user 40.

FIG. 7B illustrates a schematic view of a second step of the method for implanting a binaural cochlear implant system according to the disclosure. In this second step the surgeon performs a vertex incision 88 and a first tunneling 90 made by means of a surgical tool (see FIG. 8). The surgical tool may comprise a flexible blade provided with a sharp edge on the proximal side in order to lift off the fascia from the periosteum. This surgical tool can be made of soft plastic pebax, PMMA, PC or metal such as stainless steel for example.

FIG. 7C illustrates a schematic view of a third step of the method for implanting a binaural cochlear implant system according to the disclosure. In the third step, when the surgeon has made the tunneling 90 from the vertex incision 88 to the ipsilateral side before removing the tool (see FIG. 8), he has to attach the disposable protection 86 to the surgical tool with a suture (see FIG. 8C). Hereafter, the surgical tool can be removed from the tunneling 90 and take out the lead in vertex position 88.

FIG. 7D illustrates a schematic view of a fourth step of the method for implanting a binaural cochlear implant system according to the disclosure. In this step the surgeon performs a controlateral incision 100 and a tunneling 90' from the controlateral side to the vertex incision 88 by using a tool (see FIG. 8).

FIG. 7E illustrates a schematic view of a sixth step of the method for implanting a binaural cochlear implant system according to the disclosure. In the sixth step the surgeon attaches a disposable protection 86 to the surgical tool shown in FIG. 8 before the tool is pulled back to completely take off the lead in the controlateral position 100. The surgeon hereafter closes the vertex incision 88.

FIG. 7F illustrates a schematic view of a seventh step of the method for implanting a binaural cochlear implant system according to the disclosure. In this step the surgeon practices mastoidectomy and cochleostomy. He removes the disposable protection 86 by cutting and removing the non-absorbable suture. He has access to the fixation member and is capable of firmly fixing it with a suture attached to the bone, or with a jump and one or more implantable screws. He can now insert the controlateral electrode array into the cochlea. Finally, he closes the controlateral incision 100.

FIG. 8A illustrates a schematic view of a tool 92 according to the disclosure. The tool 92 is configured to create a tunnelling between skull and skin of a hearing aid user. FIG. 8B illustrates a close-up view of the distal portion of the tool 92 shown in FIG. 8A.

The surgical tool 92 comprises a flexible blade having a sharp edge 94 provided on its proximal side for allowing the tool to be used to lift off the fascia from the periosteum. The surgical tool 92 comprises a hole 96 provided in the distal end of the tool 92.

FIG. 8C illustrates a schematic view of the tool 92 shown in FIG. 8A attached to a disposable protection assembly 86. The tool 92 is attached to the protection assembly 86 by means of suture attached to a hole 96 provided in the tool 92 and a hole 96 provided in the protection assembly 86.

FIG. 8D illustrates a schematic view of a fixation member 106 being attached to a bone by means of suture 98. The fixation member 106 comprises a receiving section 108 configured to receive suture 98.

FIG. 8E illustrates a schematic view of a fixation member 106 being attached to a bone by means of a jump 102 and two implantable screws 104. The jump 102 is attached to a receiving section 108 of the fixation member 106.

A Cochlear Implant typically includes i) an external part for picking up and processing sound from the environment, and for determining sequences of pulses for stimulation of the electrodes in dependence on the current input sound, ii) a (typically wireless, e.g. inductive) communication link for simultaneously transmitting information about the stimulation sequences and for transferring energy to iii) an implanted part allowing the stimulation to be generated and applied to a number of electrodes, which are implantable in different locations of the cochlea allowing a stimulation of different frequencies of the audible range. Such systems are e.g. described in U.S. Pat. No. 4,207,441 and in U.S. Pat. No. 4,532,930.

In an aspect, the hearing device comprises multi-electrode array e.g. in the form of a carrier comprising a multitude of electrodes adapted for being located in the cochlea in proximity of an auditory nerve of the user. The carrier is preferably made of a flexible material to allow proper positioning of the electrodes in the cochlea such that the electrodes may be inserted in cochlea of a recipient. Preferably, the individual electrodes are spatially distributed along the length of the carrier to provide a corresponding spatial distribution along the cochlear nerve in cochlea when the carrier is inserted in cochlea.

As used, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will also be understood that when an element is referred to as being "connected" or "coupled" to another element, it can be directly connected or coupled to the other element but an intervening elements may also be present, unless expressly stated otherwise. Furthermore, "connected" or "coupled" as used herein may include wirelessly connected or coupled. As used herein, the term "and/or" includes any and all combinations of one or more of the associated listed items. The steps of any disclosed method is not limited to the exact order stated herein, unless expressly stated otherwise.

It should be appreciated that reference throughout this specification to "one embodiment" or "an embodiment" or "an aspect" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various aspects described herein. Various modifications to these aspects will be readily apparent to those skilled in the art, and the generic principles defined herein may be applied to other aspects.

The claims are not intended to be limited to the aspects shown herein, but is to be accorded the full scope consistent with the language of the claims, wherein reference to an element in the singular is not intended to mean "one and only one" unless specifically so stated, but rather "one or more." Unless specifically stated otherwise, the term "some" refers to one or more.

Accordingly, the scope should be judged in terms of the claims that follow.

LIST OF REFERENCE NUMERALS

2 External device
4 Electrode
6 Cochlea
8 Stimulator
10 Lead
12, 12' Outer ear
14 Microphone
16 Sound signal
18 Signal processor
20, 20' Electrode array
22 Battery
24 Electromagnetic coupling
26 Electronics
28, 28' Coil
30 Binaural implant
32 Ipsilateral side
34 Contralateral side
36 Incision at vertex
38 Canal in the skin
40 Hearing aid user
42 Tool for making a canal
44 Tube
46 Direction
48 Electrical wire
50, 50' Reinforcement fiber
52 Fixation member
54 Protection member
56 Proximal end
58 Hole
60 Multi-lumen tubing
62 Wire
64 Reinforcement fiber (stretchable)
66 Opening
68 Fixing structure
70 Groove
72 Protection layer
74 Sheath (knitted)
76 Mesh
78 Stop member
80 Opening
82 Rupture
84 Ipsilateral electrode array
84' Controlateral electrode array
86 Protection assembly
88 Vertical incision
90, 90' Tunneling
92 Tool
94 Edge
96 Hole
98 Suture
100 Contralateral incision
102 Attachment structure
104 Implantable screw
106 Fixation member
108 Receiving section
D Distance

The invention claimed is:

1. A binaural cochlear implant system comprising:
an implantable stimulator;
an ipsilateral cochlear implant electrode array connected to the stimulator;
a lead connected to the stimulator at a first end of the lead and connected to a contralateral binaural cochlear implant electrode array at a second end of the lead, the lead being configured to be implanted beneath the skin above the skull of a hearing aid user, wherein the lead comprises at least one electrical wire connecting the contralateral binaural cochlear implant electrode array with the stimulator, and a reinforcement fiber running along length of the at least one electrical wire, and
a fixation member at the second end of the lead fixed to the reinforcement fiber, the fixation member being configured to receive a proximal end of the contralateral binaural cochlear implant electrode array, which is connected to the at least one electrical wire.

2. The binaural cochlear implant system according to claim 1, wherein during insertion of the contralateral binaural cochlear implant electrode array, further comprising a protection member the protection member being configured to be removably attached to a distal end of the fixation member and to protectively surround the contralateral binaural cochlear implant electrode array.

3. The binaural cochlear implant system according to claim 2, wherein the protection member is arranged at a distal end of the protection member and configured to allow attaching a surgical tool configured to facilitate passage of the contralateral binaural cochlear implant electrode array beneath the skin.

4. A binaural cochlear implant system comprising:
an implantable stimulator;
an ipsilateral cochlear implant electrode array connected to the stimulator; and
a lead connected to the stimulator at a first end of the lead and connected to a contralateral binaural cochlear implant electrode array at a second end of the lead, the lead being configured to be implanted beneath the skin above the skull of a hearing aid user, wherein the lead comprises at least one electrical wire connecting the contralateral binaural cochlear implant electrode array with the stimulator, and a non-conductive reinforcement fiber running along length of the at least one electrical wire,
wherein the lead comprises a multi-lumen tubing provided with a plurality of separated through-going canals, wherein at least one of the through-going canals is configured to allow passage of the at least one electrical wire from the first end to the second end, and another of through-going canals is configured to allow passage of the reinforcement fiber from the first end to the second end, such that the reinforcement fiber is spaced apart from each of the at least one electrical wire inside the multi-lumen tubing.

5. The binaural cochlear implant system according to claim 1, wherein the lead comprises the reinforcement fiber and a secondary reinforcement fiber arranged within the lead wherein the secondary reinforcement fiber is arranged to run along the length of the reinforcement fiber and to extend beyond the fixation member.

6. The binaural cochlear implant system according to claim 1, wherein the reinforcement fiber is stretchable along its length.

7. The binaural cochlear implant system according to claim 1, wherein the reinforcement fiber comprises a stretchable mesh structure or stretchable knitted sheath.

8. The binaural cochlear implant system according to claim 5, wherein the secondary reinforcement fiber comprises a stop member attached to a distal end of the secondary reinforcement fiber, the stop member being configured to cooperate with the fixation member in response to stretching of the reinforcement fiber.

9. The binaural cochlear implant system according to claim 8, wherein the stop member is configured to restrict further stretching of the reinforcement fiber through cooperation between the stop member and fixation member once the reinforcement fiber has been stretched by a predefined allowable length.

10. The binaural cochlear implant system according to claim 1, wherein the fixation member comprises an opening configured to provide access to the reinforcement fiber for allowing cutting the reinforcement fiber when the reinforcement fiber has been stretched by the predefined allowable length.

11. The binaural cochlear implant system according to claim 1, wherein the fixation member comprises a receiving section configured to receive an attachment structure that is configured to immovably attach the fixation member to skull bone of the user.

12. The binaural cochlear implant system according to claim 11, wherein the attachment structure is selected from a group consisting of a suture that is configured to affix with the skull bone and a strip comprising at least two holes configured to receive implantable screw that is fixable to skull bone of the user.

13. The binaural cochlear implant system according to claim 1, wherein the protection member comprises:

a lumen adapted to at least partially receive the fixation member and completely receive the contralateral binaural cochlear implant electrode array and a groove adapted to receive a suture, wherein the suture is adapted to provide attachment between the protection to the fixation member.

14. A kit comprising a binaural cochlear implant system according to claim 1 and one or more of the following: protection member, suture, surgical tool, implantable screws, attachment structure.

15. The binaural cochlear implant system according to claim 1, wherein the lead comprises a multi-lumen tubing provided with a plurality of separated through-going canals configured to allow passage of the at least one electrical wire and the reinforcement fiber from the stimulator at least to the fixation member.

16. The binaural cochlear implant system according to claim 2, wherein the lead comprises a multi-lumen tubing provided with a plurality of separated through-going canals configured to allow passage of the at least one electrical wire and the reinforcement fiber from the stimulator at least to the fixation member.

17. The binaural cochlear implant system according to claim 3, wherein the lead comprises a multi-lumen tubing provided with a plurality of separated through-going canals configured to allow passage of the at least one electrical wire and the reinforcement fiber from the stimulator at least to the fixation member.

18. The binaural cochlear implant system according to claim 3, wherein the lead comprises the reinforcement fiber and a secondary reinforcement fiber arranged within the lead, wherein the secondary reinforcement fiber is arranged to run along the length of the reinforcement fiber and to extend beyond the fixation member.

19. The binaural cochlear implant system according to claim 2, wherein the lead comprises the reinforcement fiber and a secondary reinforcement fiber arranged within the lead, wherein the secondary reinforcement fiber is arranged to run along the length of the reinforcement fiber and to extend beyond the fixation member.

* * * * *